United States Patent [19]
Fujii et al.

[11] Patent Number: 5,840,685
[45] Date of Patent: Nov. 24, 1998

[54] INTRAVAGINAL DELIVERY OF BIOLOGICALLY ACTIVE POLYPEPTIDES

[75] Inventors: Takeru Fujii, Naruto; Seiichi Sako, Anan; Shigeyuki Takama, Itano-gun; Toru Hibi; Akiya Yamada, both of Takamatsu, all of Japan

[73] Assignee: Teikoku Seiyaku Co., Ltd., Kagawa, Japan

[21] Appl. No.: 899,165

[22] Filed: Jun. 15, 1992

Related U.S. Application Data

[63] Continuation of Ser. No. 315,502, Mar. 1, 1989, abandoned, which is a continuation-in-part of Ser. No. 167,163, Mar. 11, 1988, abandoned.

[51] Int. Cl.$^6$ .............................. A61K 38/00; C07K 7/60; C07K 7/36; C07K 14/00
[52] U.S. Cl. ............................ 514/12; 530/324; 530/307
[58] Field of Search ................................. 530/324, 307; 514/12

[56] References Cited

U.S. PATENT DOCUMENTS

| | | | |
|---|---|---|---|
| 3,888,838 | 6/1975 | Immer et al. | 530/313 |
| 3,917,825 | 11/1975 | Matsuzawa et al. | 514/15 |
| 4,010,125 | 3/1977 | Schally et al. | 530/313 |
| 4,018,726 | 4/1977 | Schally et al. | 530/313 |
| 4,083,967 | 4/1978 | Beddell et al. | 514/15 |
| 4,234,571 | 11/1980 | Nestor et al. | 530/313 |
| 4,609,640 | 9/1986 | Morishita et al. | 514/12 |
| 4,659,696 | 4/1987 | Hirai et al. | 514/15 |
| 4,670,419 | 6/1987 | Uda et al. | 514/16 |
| 4,690,952 | 9/1987 | Kagatani et al. | 514/2 |

FOREIGN PATENT DOCUMENTS

| | | |
|---|---|---|
| 0183527 | 6/1986 | European Pat. Off. . |
| 0193372 | 9/1986 | European Pat. Off. . |
| 56-122309 | 9/1981 | Japan . |
| 62-36498 | 8/1987 | Japan . |
| 2127689 | 4/1984 | United Kingdom . |
| 2193631 | 2/1988 | United Kingdom . |

OTHER PUBLICATIONS

Azaz et al, Chem. Abst. 96:74626N (1982).
Hirai, International Journal of Pharmaceutical, 174–184, 1981.
Muranishi, "Absorption Barriers and Absorption Promoters in the Intestine", Topics in Pharmaceuticals Sciences (1987), pp. 445–455.
Jerusalem University, IL 54041, "Pharmaceutical composition for enteral or vaginal application" (1981).
Morimoto, et al., "Effect of non–ionic surfactants in a polyacrylic acid gel base on the rectal absorption of [Asu 1,7]–eel calcitonin in rats", J. Pharm. Pharmacol., vol. 37 (1985), pp. 759–760.
Okada, "Vaginal Administration of a Potent Luteinizing Hormone–Releasing Hormone Analog (Leuprolide)", J. Takeda Res. Lab., 42 (½) (1983), pp. 150–208.
Touitou, et al., "New hydrophilic vehicle enabling rectal and vaginal absorption of insulin, heparin, phenol red and gentamicin", J. Pharm. Pharmac., vol. 30 (1978), pp. 662–663.
Saito, et al., "Stimulation of Luteinizing Hormone (LH) and Follicle–Stimulating Hormone by [D–LEU$^6$, DES–GLY$^{10}$–NH$_2$]–LH–Releasing Hormone Ethylamide After Subcutaneous, Intravaginal, and Intrarectal Administration To Women", Fertility and Sterility, vol. 28, No. 3 (1977), pp. 240–245.
Okada, et al., "Vaginal Absdorption of a Potent Luteinizing Hormone–Releasing Hormone Analogoue (Leuprolide) in Rats II: Mechanism of Absorption Enhancement with Organic Acids", Journal of Pharmaceutical Sciences, vol. 72, No. 1 (1983), PP. 75–78.
Okada, Journal of Pharmaceutical Sciences, 71, No. 12, 1366–1371 (1982).

Primary Examiner—Cecilia J. Tsang
Assistant Examiner—S. G. Marshall
Attorney, Agent, or Firm—Burns, Doane, Swecker & Mathis, L.L.P.

[57] ABSTRACT

Pharmaceutical compositions of matter adapted for intravaginal administration comprise a biologically active polypeptide, an absorption promoter, such as an anionic and/or nonionic surfactant or a nonionic surfactant and an aliphatic carboxylic acid, optionally an animal and/or vegetable protein and a nontoxic pharmaceutically acceptable carrier or diluent therefor, in a formulation suitable for intravaginal administration. Preferred compositions comprise calcitonin as the biologically active polypeptide. Preferred absorption promoters are anionic surfactants, e.g., sodium lauryl sulfate, and the combination absorption promoter of a nonionic surfactant and a medium chain aliphatic carboxylic acid or its salt, e.g. polyoxyethylenealkylphenylether and a medium chain aliphatic carboxylic acid.

8 Claims, 8 Drawing Sheets

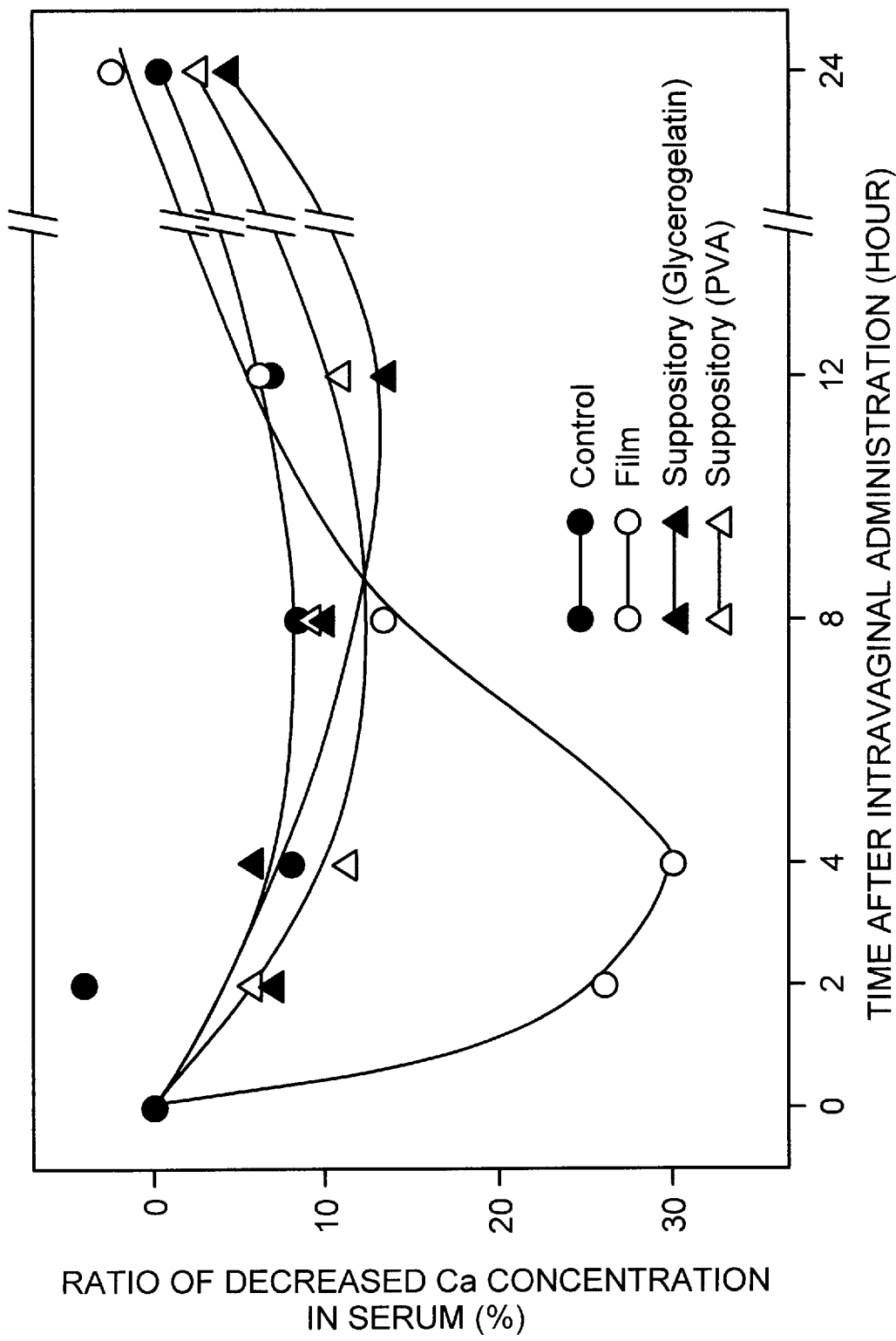

INTRAVAGINAL DELIVERY OF BIOLOGICALLY ACTIVE POLYPEPTIDES

CROSS-REFERENCE TO RELATED APPLICATIONS

This application is a continuation of application Ser. No. 07/315,502, filed Mar. 1, 1989, now abandoned, which is a continuation-in-part of application Ser. No. 167,163 filed Mar. 11, 1988, now abandoned, by Takeru Fujii, Seiichi Sako and Shigeyuki Takama, incorporated by reference herein in its entirety and relied upon.

BACKGROUND OF THE INVENTION

1. Field of the Invention

The present invention relates to pharmaceutical compositions of matter adapted for intravaginal administration comprising a biologically active polypeptide, an absorption promoter, optionally an animal and/or vegetable protein and a nontoxic pharmaceutically acceptable carrier or diluent therefor, in a formulation suitable for intravaginal administration; and to the use of such compositions to treat a variety of disease states. The invention further relates to a method for enhancing the absorbability of an intravaginally administered biologically active polypeptide and to a method for enhancing the storage stability and reducing the mucosal irritation of an intravaginal pharmaceutical formulation comprising a biologically active polypeptide.

2. Description of the Art

Polypeptide hormones such as insulin and calcitonin are water-soluble, relatively small molecular weight compounds which are readily decomposed by gastric juices and by intestinal proteinases such as pepsin and trypsin. As a result, when these polypeptides are orally administered, they are barely absorbed and produce no effective pharmacological action. In order to obtain the desired biological activity, the polypeptides are at present usually dispensed in injectable dosage forms. However, the injectable route is inconvenient and painful to the patient, particularly when administration must occur on a regular and frequent basis; consequently, efforts have focused recently on alternative methods for administration of the polypeptide hormones.

Hirai et al U.S. Pat. No. 4,659,696 and Uda et al U.S. Pat. No. 4,670,419 (TAKEDA CHEMICAL INDUSTRIES, LTD.) describe pharmaceutical compositions for nasal, vaginal or rectal administration comprising a hydrophilic therapeutic agent poorly absorbable in the gastrointestinal tract, together with cyclodextrin. Among the therapeutic agents present in the compositions are polypeptides, e.g., insulin, LH-RH analogs, oxytocin and TRH. The cyclodextrin is preferably alpha-cyclodextrin. Various pharmaceutical additives may also be present in the formulations.

Morishita et al U.S. Pat. No. 4,609,640 (TOYO JOZO COMPANY, LTD.) describes a therapeutic composition for rectal or vaginal administration, said to have excellent absorption properties, which contains a water-soluble therapeutic agent and a water-soluble chelating agent of a particular type. The therapeutic agent may be a peptide hormone such as insulin, somatostatin, calcitonin, etc. Water-soluble base polymers having no chelating activity, such as gelatin, casein, albumin and globulin, may be employed if used in conjunction with a chelating agent of low molecular weight, i.e., one of a number of polycarboxylic acids or the like. Other conventional ingredients for such dosage forms, e.g., a surfactant, may also be present.

TEIJIN LIMITED's European Patent Publication No. 0193372 discloses a nasal powder comprising a physiologically active polypeptide, a quaternary ammonium compound and a lower alkyl ether of cellulose, purportedly having excellent preservability and chemical stability. Preferred powders comprise insulin or calcitonin, benzalkonium chloride and hydroxypropyl cellulose. Various conventional additives may also be present, e.g., lubricants, waxes, binders, diluents, coloring agents, odor improvers, antioxidants, bulk fillers, isotonic agents and surfactants.

YAMANOUCHI PHARMACEUTICAL CO. LTD.'s European Patent Publication No. 0183527 describes an absorbable nasal calcitonin medicament comprising calcitonin and at least one absorption enhancer selected from benzyl acid and salts thereof, capric acid and salts thereof, polyethylene glycol 400, pyridoxal and salts thereof, malic acid and salts thereof and pyrophosphoric acid and salts thereof. Other ingredients conventional for nasal formulations may be added. Use of one of the specific absorption enhancers is said to improve efficiency of absorption across the membrane of the nasal cavity. The patent publication indicates that earlier attempts to improve the nasal absorbability of a large polypeptide such as calcitonin utilized surface active agents as absorption enhancers. The earlier work employed both amphoteric and cationic surface active agents, especially the nonionic surface active agent polyoxyethylene lauryl ether; unfortunately, the preferred ether type surface active agent is said to promote drug absorption by destroying the nasal membrane.

SANDOZ LTD.'s U.K. Patent Application No. 8326436, published as GB 2127689A, relates to pharmaceutical compositions for nasal administration comprising calcitonin, benzalkonium chloride and/or a surfactant suitable for nasal application, in a liquid diluent or carrier suitable for application to the nasal mucosa. When the compositions comprise a surfactant, it is preferably a non-ionic one, most preferably a polyoxyalkylene higher alcohol ether. Improved bioavailability and good stability are said to be achieved by these calcitonin inhalation compositions.

Matsuzawa et al U.S. Pat. No. 3,917,825 (TAKEDA CHEMICAL INDUSTRIES, LTD.) discloses pharmaceutical preparations for rectal or vaginal administration of LH-RH or its analogs. The nona- or decapeptide is dispersed homogeneously in an oleaginous base (e.g., oil, wax or fatty acid triglyceride) preferably containing a non-ionic surfactant such as a polyoxyethylene higher alcohol ether. Administration of nonapeptides and decapeptides by a variety of routes, including intravaginal, is described in numerous patents and publications, e.g., Beddell et al U.S. Pat. No. 4,083,967; Immer et al U.S. Pat. No. 3,888,838; Nestor et al U.S. Pat. No. 4,234,571; Schally et al U.S. Pat. No. 4,010, 125; Schally et al U.S. Pat. No. 4,018,726; and Saito et al, *Fertility and Sterility*. Vol. 28, No. 3, March 1977, 240–245.

Okada et al, *J. Pharm. Sci.*, Vol. 72, No. 1, January 1983, 75–78, describe vaginal absorption of a potent LH-RH analog (leuprolide), of LH-RH itself and of insulin. Absorption enhancement is provided by use of organic acids. The enhancing potency appears to correlate with the chelating ability of the organic acids. See also Okada, *J. Takeda Res. Lab.* 42 (½), 150 (1983).

Touitou et al, *J. Pharm. Pharmac.*, 1978, 30, 663, have developed a hydrophilic vehicle for rectal or vaginal administration of insulin, heparin, phenol red and gentamicin comprising the non-ionic surfactant, Cetomacrogol 1000 (polyethylene glycol 1000 monocetyl ether) in combination with polyethylene glycols. JERUSALEM UNIVERSITY's IL 54041 directed to pharmaceutical compositions containing a non-ionic surfactant for enteral or vaginal administration of peptide hormone or heparin appears to be related to the same work.

Morimoto et al, *J. Pharm. Pharmacol.* 1985, 37, 759–760, have reported on the effect of non-ionic surfactants, polyoxyethylene sorbitan monooleate and polyoxyethane 9 lauryl ether, on the enhancement of polyacrylic acid gel base in the rectal absorption of a semisynthetic analog of eel calcitonin. The polyacrylic acid gel base had been found earlier to improve absorption of insulin by rectal, vaginal and nasal routes and that of calcitonin by rectal and nasal routes. Earlier reports also indicated that the absorption of poorly absorbable drugs can be enhanced by co-administering the drug with enamine, carboxylic acid and surface-active agents.

TEIJIN's JP 56122309 also JP Patent Bulletin (B2) SH062-36498, describes calcitonin compositions for rectal administration in which calcitonin and a surfactant (cholic acid, saponin, phospholipid, polyoxyethylene alkyl ether, glycerin fatty acid ester, sorbitan fatty acid ester or the like) are homogeneously dispersed in a suppository base.

Muranishi, S., "Absorption Barriers and Absorption Promoters in the Intestine", in *Topics in Pharmaceutical Sciences* 1987, describes the absorption of drugs through the intestine using a variety of compositions which aid in the absorption of the drug through the cells that line the mucosal surface. A mixed-micelle system was disclosed which involved the use of an unsaturated aliphatic carboxylic acid with a nonionic surfactant.

Nevertheless, the alternative methods investigated thus far generally suffer from a number of disadvantages. Thus, these methods require higher doses than those needed for injectable administration and result in large fluctuations in drug levels upon absorption. Moreover, it would be desirable to provide dosage forms of polypeptides which are storage stable, which are non-irritating to and readily absorbed by the target mucosa, and which are stable at the site of administration. While numerous attempts have been made to find alternatives to parenteral administration of biologically active polypeptides such as insulin and calcitonin, the art as a whole has not addressed the related problem that biologically active peptides tend to lose their biological activity during storage. The need to produce stable pharmaceutical dosage forms containing biologically active polypeptides is an important problem in manufacturing these drugs. Moreover, in the search for alternatives to administration by injection, the art as a whole has not taught how to avoid enzymatic decomposition of the polypeptides both at their administration sites and during the absorption process.

SUMMARY OF THE INVENTION

The present inventors have now developed a non-injectable pharmaceutical dosage form containing a biologically active polypeptide such as insulin or calcitonin, aimed at alleviating the pain of injection and minimizing decomposition of the polypeptide.

In one aspect, the present invention thus provides a pharmaceutical composition of matter adapted for intravaginal administration comprising a biologically active polypeptide, an absorption promoter such as an anionic and/or nonionic surfactant or a nonionic surfactant and medium chain aliphatic carboxylic acid or salt thereof, optionally an animal and/or vegetable protein and a nontoxic pharmaceutically acceptable carrier or diluent therefor, in a formulation suitable for intravaginal administration.

In another aspect, the present invention provides use of the aforementioned compositions in the treatment of various disease states.

In yet another aspect, the present invention provides a method for enhancing the absorbability of an intravaginally administered biologically active polypeptide, said method comprising co-administering said polypeptide with an absorption promoter such as an anionic and/or nonionic surfactant or a nonionic surfactant and a medium chain aliphatic carboxylic acid or salt thereof, and optionally an animal and/or vegetable protein, via the vaginal route.

In still another aspect, the present invention provides a method for enhancing the storage stability of an intravaginal pharmaceutical formulation comprising a biologically active polypeptide, said method comprising incorporating into said pharmaceutical formulation an absorption promoter such as an anionic and/or nonionic surfactant or a nonionic surfactant and a medium chain aliphatic carboxylic acid or salt thereof, and optionally an animal and/or vegetable protein.

In another aspect, the present invention provides a method of administering an intravaginal pharmaceutical formulation with little or no irritation to the mucosal membrane by co-administering a polypeptide with an absorption promoter such as an anionic and/or nonionic surfactant or a nonionic surfactant and a medium chain aliphatic carboxylic acid or salt thereof, and optionally an animal and/or vegetable protein.

Still further, the present invention provides a method for inhibiting vaginal protease at the site of administration of a biologically active polypeptide, said method comprising co-administering said polypeptide with an absorption promoter such as anionic and/or nonionic surfactant or a nonionic surfactant and a medium chain aliphatic carboxylic acid, via the vaginal route.

BRIEF DESCRIPTION OF THE DRAWINGS

FIG. 8 is a graph showing that the serum calcium decreased correspondingly with the increase of serum salmon calcitonin (S-CT) following the vaginal suppository administration of S-CT, Nonidet P-40 and sodium caprate and BSA to young, oophorectomized female rats.

DETAILED DESCRIPTION OF THE PREFERRED EMBODIMENTS OF THE INVENTION

Figure 1:
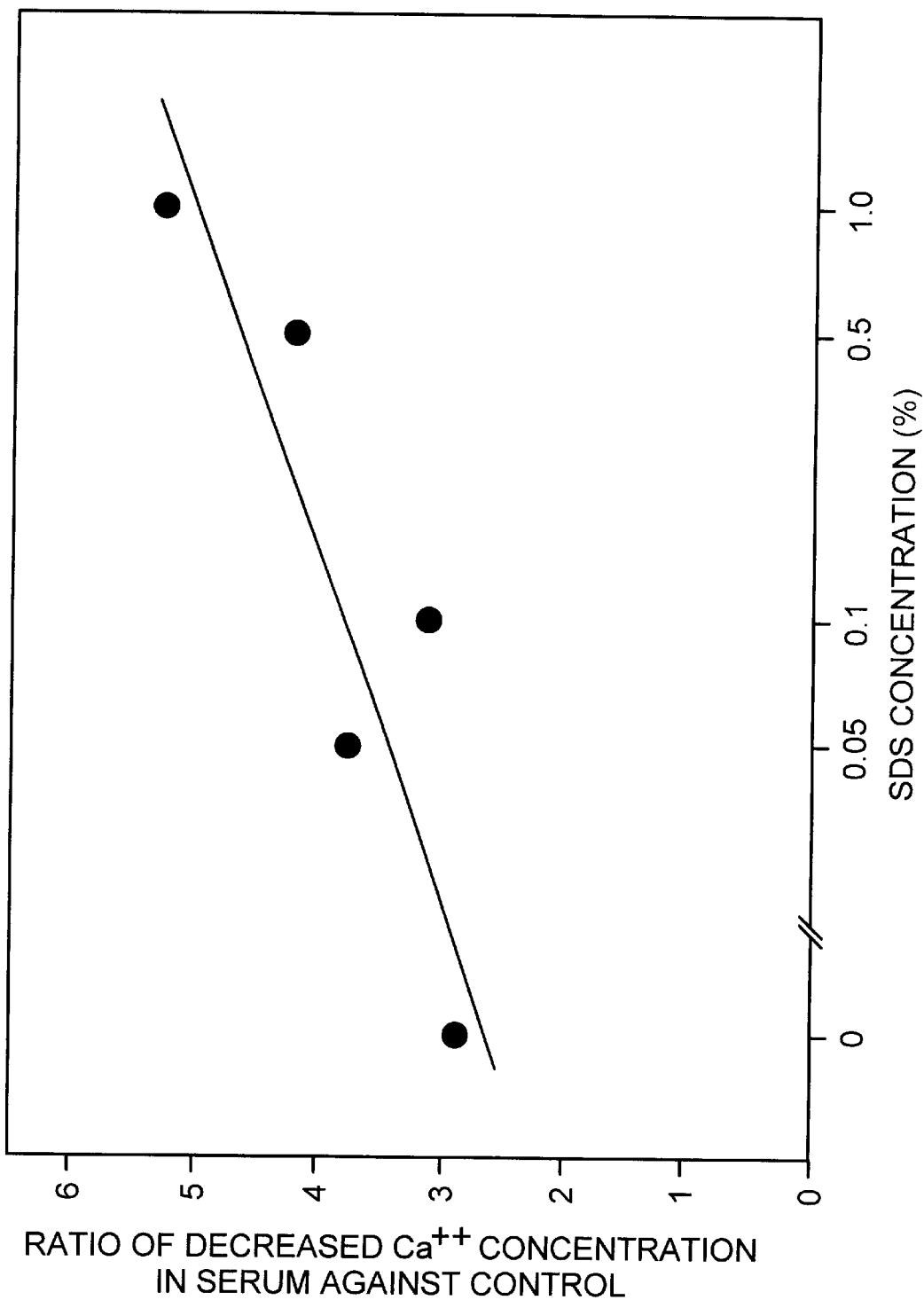
FIG. 1 is a plot showing the absorption enhancing effects of increasing concentrations of sodium lauryl sulfate (SDS) on porcine calcitonin administered intravaginally to young, oophorectomized female rats.

Biologically active polypeptides for use in the present invention are polypeptides of relatively small molecular weights. Exemplary preferred biologically active polypeptides for use herein are insulin, angiotensin, vasopressin, desmopressin, LH-RH (luteinizing hormone-releasing hormone), somatostatin, calcitonin, glucagon, somatomedin, oxytocin, gastrin, secretin, h-ANP (human artrial natriuretic polypeptide), ACTH (adrenocorticotropic hormone), MSH (melanocyte stimulating hormone), beta-endorphin, muramyl dipeptide, enkephalin, neurotensin, bombesin, VIP (vasactive intestinal peptide), CCK-8, PTH (parathyroid hormone), CGRP (calcitonin gene related peptide), endothelin, TRH (thyrotropin releasing hormone) and the like. The various polypeptides for use herein include not only the naturally occurring polypeptides themselves but also pharmacologically active derivatives and/analogs thereof. Thus, for example, calcitonin intended for use in the present invention includes not only naturally occurring products such as salmon calcitonin, human calcitonin, porcine calcitonin, eel calcitonin and chicken calcitonin, but also analogs such as [$Asu^{1,7}$]-eel calcitonin or elcatonin, a product of Toyo Jozo Company, Ltd., as well. Similarly, LH-RH for use herein includes not only the naturally occurring product but also the pharmaceutically active derivatives and analogs thereof such as described in various patents and publications referenced hereinabove, e.g. Matsuzawa et al U.S. Pat. No. 3,917,825. Especially preferred polypeptides for use in the present invention include calcitonin, insulin, ACTH, LH-RH, PTH, CGRP and somatomedin.

The amount of the biologically active peptide in the intravaginal pharmaceutical preparations will vary, depending upon the particular polypeptide employed, but will be an amount sufficient to elicit the desired pharmacological effect. Thus, for example, when the selected polypeptide is calcitonin, such will be present in an amount sufficient to treat a condition such as Paget's disease or hypercalcemia or osteoporosis. A typical preparation may contain, for example, from about 0.01 to about 0.04 I.U./mg for porcine calcitonin. In the case of insulin, an amount sufficient to control blood sugar levels and thus to treat diabetes will typically be employed; in the case of LH-RH or analog thereof, an amount sufficient to treat various disorders of the female reproductive system, an amount sufficient to have a contraceptive effect, or an amount sufficient to elicit any other known biological response to LH-RH will be used, in the case of PTH, CGRP, somatomedin or analog thereof, an amount sufficient to treat various disorders of bone metabolism will be used; and so on for the other biologically active peptides contemplated by the present invention.

The absorption promoters for use in the present invention may be selected from an anionic and/or nonionic surfactant and a combination type absorption promoter, e.g., a nonionic surfactant plus a medium chain aliphatic carboxylic acid and its salts.

The anionic and nonionic surfactants for use in the present invention may be used singly or in a combination of two or more from one or both categories. Preferred anionic surfactants include sodium lauryl sulfate, polyoxyethylenalkylphenyl ether sodium sulfate, sodium alkylnaphthalenesulfonate and sodium alkylbenzene sulfonate, as well as other sulfuric acid esters of higher primary alcohols and other salts of alkylnaphthalenesulfonic acid. Particularly preferred anionic surfactants are sodium lauryl sulfate and sodium alkylnaphthalenesulfonate (Pelex NBL™), most especially sodium lauryl sulfate. These anionic surfactants are usually in the form of their alkali metal salts. Preferred nonionic surfactants are exemplified by sorbitan fatty acid esters, polyoxysorbitan fatty acid esters and polyoxyalkylene higher alcohol ethers. The most preferred nonionic surfactant is polyoxyethylene (23) lauryl ether (Emulgen, a registered trademark).

The combination absorption promoter is a nonionic surfactant and a medium chain aliphatic carboxylic acid or its salt. The nonionic surfactant is preferably a polyoxyethylenealkylphenylether. The polyoxyethylene component can be depicted as $(OCH_2CH_2)_n$ where n ranges from 5 to 30. The alkyl component is preferably a $C_8$–$C_9$ straight chain alkyl, i.e., polyoxyethyleneoctylphenylether or polyoxyethylenenonylphenylether. The more preferred polyoxyethylenealkylphenylethers are polyoxyethylene (9) or (10) or (30) octylphenylether, polyoxyethylene (10) or (15) or (20) nonylphenylether. A particularly preferred polyoxyethylenealkylphenylether is Nonidet P-40, a registered trademark for polyoxyethylene (9) octylphenylether by Sigma Chemical Company.

The medium chain-aliphatic carboxylic acid is preferably saturated and may be depicted as R-COOH where R is preferably a $C_5$–$C_{15}$ straight chain saturated alkyl. Preferred medium chain aliphatic carboxylic acids are sodium caproate, sodium caprylate, sodium caprate and sodium laurate. The most preferred medium chain aliphatic carboxylic acid salt is sodium caprate.

The amount of the absorption promoter in the intravaginal pharmaceutical preparation of this invention will vary, depending upon the particular absorption promoter selected. Generally speaking, however, the usual concentration of absorption promoter such as an anionic and/or nonionic surfactant or the combination of a nonionic sufactant such as polyoxyethylenealkylphenylether and medium chain aliphatic carboxylic acid or its salt is between about 0.01 and 5% (w/v %), preferably between about 0.05 and 2% (w/v %).

The animal and vegetable proteins used in the practice of the present invention are preferably selected from among proteins which have previously been used in food or medical preparations. Preferred examples of animal protein are albumin, e.g., bovine serum albumin (BSA) or human serum albumin (HSA), casein, gelatin and the like. Albumin is particularly preferred. Examples of vegetable proteins contemplated for use herein are gluten, zein, soybean protein and the like. Either animal or vegetable protein may be employed, or a combination of an appropriate ratio of animal protein and vegetable protein may be used.

The animal or vegetable protein is merely optional in the practice of the present invention. The protein is only necessary when the biologically active polypeptide or derivative thereof is unstable. The stability of the various polypeptides are well known to those in the art. Elcatonin, for instance, is eel calcitonin which has been modified to improve the stability. Thus, a protein is not essential in a composition containing elcatonin. Natural eel calcitonin, on the other hand, is not as stable as elcatonin and an animal or vegetable protein must be present in the composition to maintain the stability of the polypeptide. Most polypeptides and polypeptide derivatives are unstable. Reference may be made to standard textbooks and manufacturer specifications to describe the stability of a particular polypeptide.

The amount of the animal or vegetable protein used in the composition of the present invention is an amount sufficient to maintain the stability of the polypeptide. The amount of the animal or vegetable protein generally ranges from about 0.001 to 25% (w/v %) depending on the polypeptide being stabilized.

Administration of the formulation of the present invention can be via any of the accepted modes of vaginal administration. The intravaginal pharmaceutical preparation of this invention is typically a liquid, gel (preferably highly viscous), cream, suppository, film, tablet, soft capsule or tampon-type device consisting of a biologically active polypeptide, absorption promoter and optionally an animal or vegetable protein. The intravaginal pharmaceutical preparation of this invention can be prepared by dissolving the polypeptide, absorption promoter and protein in either purified water, physiological saline solution or a buffered solution as a carrier or diluent therefor and then formulate that mixture into each dosage form.

Since the pH of the intravaginal pharmaceutical preparation of this invention is desirably as close as possible to the pH of the inner vagina, after the biologically active polypeptide, absorption promoter and optionally animal or vegetable protein are dissolved in purified water or physiological saline solution or buffered solution, the pH of the preparation is adjusted to a pH between 3 and 7, preferably between 4 and 6. The chemicals used for adjusting the pH are known acids or bases which are nontoxic and non-irritating to humans, preferred examples being organic acids such as acetic acid and citric acid, and weak bases such as sodium bicarbonate and sodium acetate.

In order to improve the properties and appearance of the pharmaceutical preparation of the present invention, one or more excipients, coloring agents, isotonic agents and anti-oxidants may be added to the intravaginal pharmaceutical preparation of this invention, for example, excipients such as starch, dextrin, mannitol, sorbitol, cyclodextrin and tragacanth, coloring agents such as beta-carotene, red color No. 2 and blue color No. 1, isotonic agents such as sodium chloride and glucose, and antioxidants such as ascorbic acid and erythorbic acid and their salts or esters. Actual methods of preparing such dosage forms are known or will be apparent, to those skilled in the art. For example, see *Remington's Pharmaceutical Sciences,* 17th edition, 1985, ed. Alfonso R. Gennaro, Mack Publishing Company, Easton, Pa. 18042.

The nature of the excipient(s) will preferably aid in the manufacture of the dosage form selected. As will be demonstrated hereinafter, certain dosage forms provide a more extended release of the biologically active polypeptide. These extended release dosage forms are particularly useful and offer increased flexibility in the administration of the polypeptide.

When the compositions according to the invention are prepared in suppository form, typical suppository bases will include triglycerides (for example Witepsol, a product of Dynamit Nobel), polyethylene glycols, glycerogelatins, polyvinyl alcohol (PVA), and the like. Suppository bases selected from triglycerides and the like will provide a "quick-release" suppository, whereas suppositories formed from glycerogelatin and the like will provide suppositories having more sustained release characteristics.

An aqueous preparation containing the biologically active peptide can be mixed with a suppository base using a mechanical mixing device such as a Vortex mixer at a suitable temperature to allow the suppository base to become fluid and then the mixture can be cooled in a suppository mold.

When the compositions according to the invention are prepared in film form, typical film bases may include:
  hydrophilic polymers such as polyvinyl alcohol, chitosan, polyhydroxyethylmethacrylate, glucomannan, pullulan and the like; and/or
  hydrophobic polymers such as ethylcellulose, polyacrylate ester, for example, Eudragit, a registered trademark of Röhm, Pharma GmbH, silicone and the like.

For making a film, an aqueous preparation of the biologically active peptide can be mixed with a film base such as hydroxypropylmethylcellulose, chitosan, pullulan, glucomannan, polyacrylate ester and then it can be cast and evaporated (dried).

When the compositions according to the present invention are prepared in gel form, typical gel bases may include:
  anionic polymers such as polyacrylic acid sodium salt, carboxymethylcellulose sodium salt and the like; and
  nonionic polymers such as polyvinyl alcohol, polyoxyethylene-propyleneglycol block copolymer, hydroxypropylcellulose, hydroxypropylmethylcellulose, hydroxyethylcellulose and so on. The gel formulations will invariably display quick-release activity.

For making a highly viscous gel preparation, a known viscosity enhancer may be added as needed. Some examples of suitable viscosity enhancers include cellulose lower alcohol ether, polyvinyl alcohol, polyvinyl pyrrolidone (PVP), polyoxyethyleneoxypropyleneglycol block copolymer (Pluronic™), and the like.

When a cream-type dosage form is prepared, both water-in-oil type cream and oil-in-water type cream can be prepared with the compositions according to the invention. Again, cream formulations will display quick-release activity.

When the compositions according to the present invention are prepared in tablet form, it should first be noted that both disintegrating and non-disintegrating tablets can be prepared. For disintegrating tablets, a strong disintegrant is preferred, such as PVP-XL, Ac-di-sol (a registered trademark of FMC Corporation) explotab, HPC-L and the like. For non-disintegrating tablets, there is needed a base capable of forming in the vagina a hydrogel matrix for the compositions of the invention. Such bases include glucomannan, alginic acid and its calcium salt, pectin, hydroxypropylmethylcellulose and the like. The disintegrating tablets provide quick-release action, whereas the non-disintegrating tablets usually provide sustained release action.

For making a tablet, the aqueous preparation containing the biologically active peptide can be mixed well with a suitable excipient such as a filler, binder and/or disintegrant and then dried, and further excipients such as a lubricant may be added, if necessary. The final mixture nay be compressed into a tablet by a tabletting machine. In addition, foaming agents such as sodium bicarbonate as a carbonate agent and citric or tartaric acid as a acidifying agent may be used alone or in combination for the disintegrating tablets, if necessary.

For making a soft capsule, an oily or polyethyleneglycol formulation containing the biologically active peptide may be incorporated into a soft capsule gel.

For making a tampon-type device, several methods may be used. For instance, a tampon shaped core of silicone resin may be covered with a polymer film such as chitosan and a polyacrylate-methacrylate copolymer containing a biologically active peptide.

Further information concerning preparation of the various intravaginal dosage forms may be found in *Remington's Pharmaceutical Sciences*, supra. When the pharmaceutical preparation of the present invention is administered intravaginally, the biologically active polypeptide is readily and effectively absorbed through the vaginal mucosa and exhibits its characteristic biological activity. Furthermore, the biologically active polypeptide, especially calcitonin or insulin, is stable in this preparation and unchanged after a long period of storage. (When appropriate, the compositions of the invention are stored in a cool place to secure their stability.) Moreover, the intravaginal preparation of the invention is not irritative to the vaginal mucosa. Still further, it has been surprisingly discovered that absorption promotions, such as anionic and/or nonionic surfactants act as inhibitors to vaginal proteinase when incorporated in the compositions of this invention; hence, the biologically active polypeptide is stable at its administration site.

In order further to illustrate the present invention and the advantages thereof, the following specific examples are given, it being understood that same are intended only as illustrative, not limitative.

EXAMPLE 1

Absorption-Enhancing Effect of Sodium Lauryl Sulfate on Calcitonin

Oophorectomy was performed on 5- to 6-week old female Wister rats which, after about one month, were used in this experiment as an animal model for postmenopausal women.

To 20 I.U. porcine calcitonin, 3 mg of bovine serum albumin (BSA) was added. Sodium lauryl sulfate (hereinafter called "SDS") was then added to the above-prepared mixture to make 0.05, 0.1, 0.5 and 1 w/v % concentrations, respectively. The mixtures of different SDS concentrations were then each diluted with 0.1M acetic acid/sodium acetate buffer solution (pH 5.0) to make 1 ml calcitonin solutions. Rats were anesthetized with ether, and a required amount of blood was taken from the right external jugular vein before the administration of calcitonin. After a small cotton ball was inserted into the vagina of the rat, each 50 microliters of calcitonin solution of different SDS concentrations was administered. Blood was again extracted 2 hours after calcitonin administration.

After the separation of blood serum, serum calcium concentration was determined with a Calcium C test kit, a registered trademark at Wako Chemical in Japan. The results are depicted in FIG. 1. The ratio of decreased serum calcium concentration against the control, which was treated with the preparation without SDS, was increased correspondingly with increasing concentration of SDS in the preparation.

EXAMPLE 2

Dose Response of Calcitonin Absorption From Vaginal Mucosa

Oophorectomized menopausal model rats were used in this experiment, similarly to Example 1.

Figure 2:
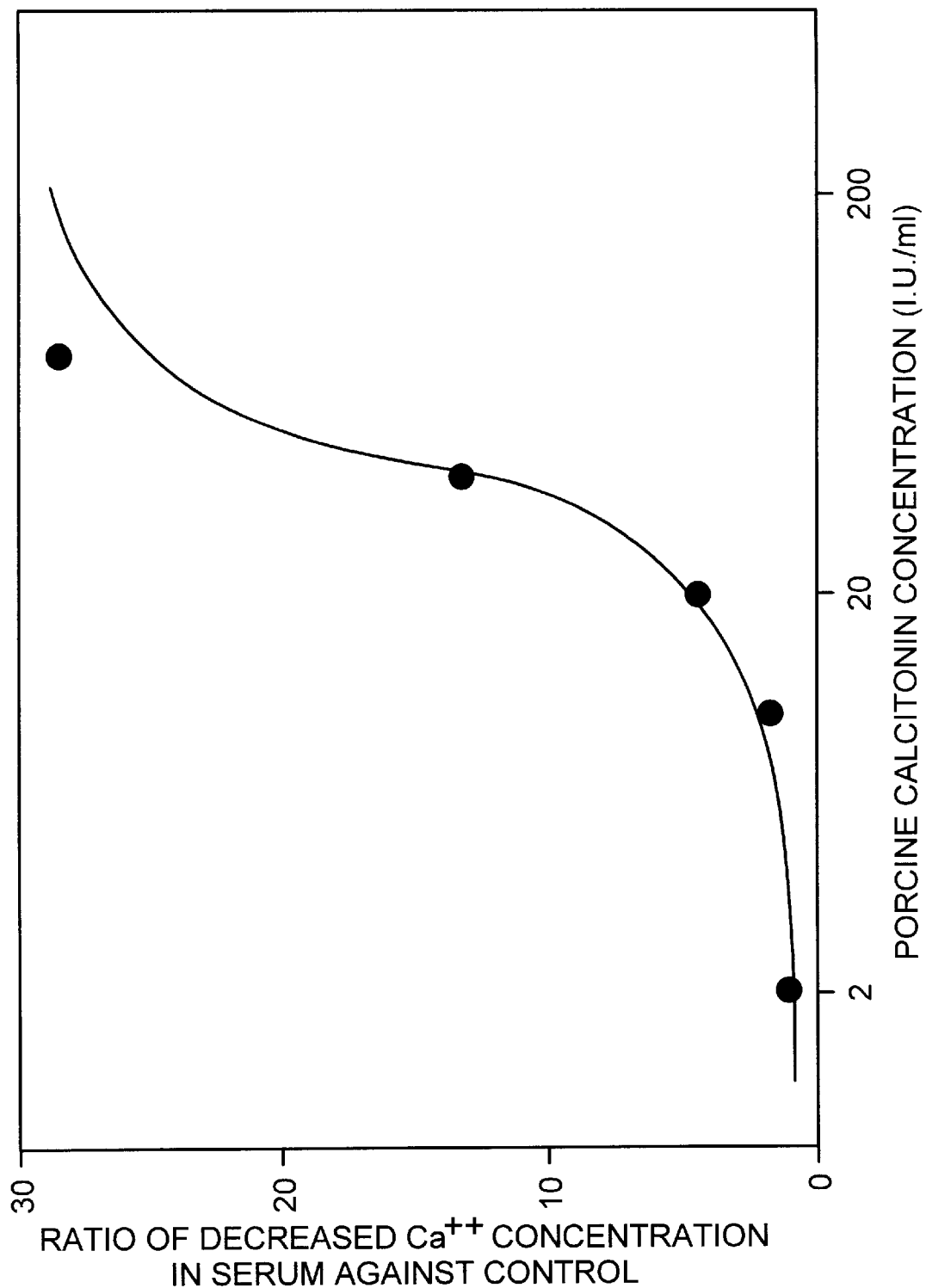
FIG. 2 is a dose response curve of porcine calcitonin absorption from the vaginal mucosa of young, oophorectomized female rats.

Bovine serum albumin was added to each 1 ml of 2, 10, 20, 40 and 80 I.U./ml of porcine calcitonin dissolved in acetic acid buffer solution (pH 5.0) to make 3 mg/ml. Then, SDS was added to each solution to make 1 w/v %. Similarly to Example 1, these preparations containing different concentrations of calcitonin were administered intravaginally to the rats, and the serum calcium concentration was determined. The ratio of decreased serum calcium against control exhibited an increase proportional to the increase of calcitonin concentration of the preparation administered. The largest ratio of decreased serum calcium against control noted in this experiment was 30%. In this experiment, it was found that the serum calcium concentration could be controlled by adjusting the dosage of calcitonin administered. See FIG. 2.

EXAMPLE 3

Evidence of the Absorption of Calcitonin Through Vaginal Mucosa

This experiment was performed to confirm that calcitonin was actually absorbed through vaginal mucosa using the intravaginal dosage form of this invention.

Figure 3:
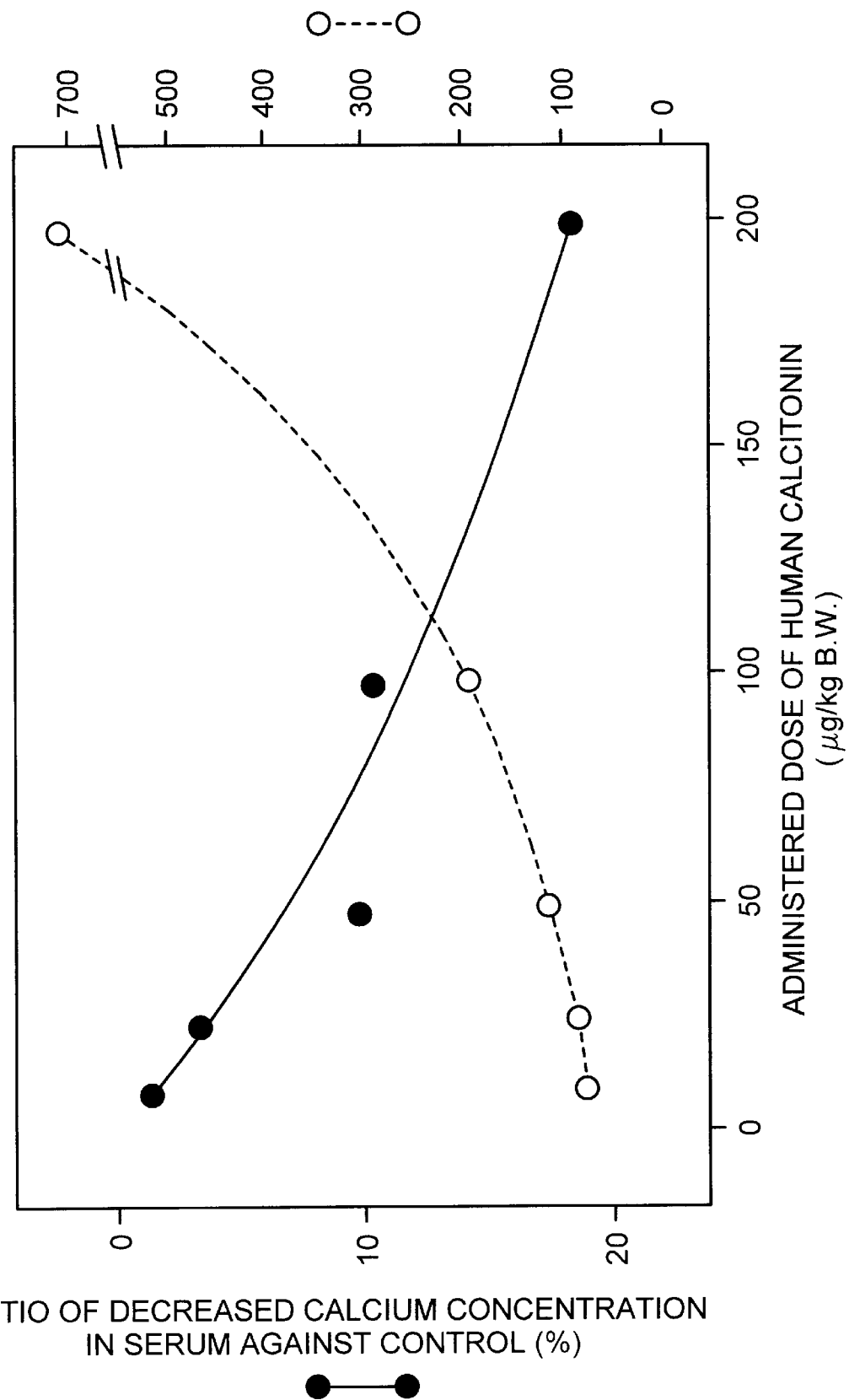
FIG. 3 is a graph showing that serum calcitonin increased proportionally to the increase of the dosage of calcitonin administered intravaginally, and serum calcium decreased correspondingly with increase of calcitonin dosage, following administration of human calcitonin to young, oophorectomized female rats.

Similarly to Examples 1 and 2, oophorectomized rats were used in this experiment. 1000 micrograms of Human calcitonin (HCT) was dissolved in 1 ml of 0.1M acetate buffer (pH 5) containing 0.3 w/v % bovine serum albumin and 1 w/v % SDS. 10, 25, 50, 100 and 200 micrograms of HCT (protein weight) in solution per 1 kg body weight of rats were taken out of the HCT solution mentioned above, and each portion of the HCT solution was diluted up to 50 microliters with 0.1M acetate buffer (pH 5) containing 0.3% (w/v %) bovine serum albumin and 1 w/v % SDS. Each 50 microliters of HCT solution with a different amount of HCT was administered into the vagina with a small cotton ball. Two hours after drug administration, blood was extracted from the right external jugular vein of the anesthetized rat, and serum calcium was determined with a Calcium C test kit. Serum calcitonin was also determined by a radioimmunoassay method (RIA method), using human calcitonin antibody. The results showed that. serum calcitonin increased proportionally to the increase in the dosage of calcitonin administered into the vagina, and serum calcium decreased correspondingly with increase in calcitonin dosage. This result implied that the absorption of human calcitonin and its biological activity exhibited dose dependent response when the intravaginal preparation of this invention was administered. See FIG. 3.

EXAMPLE 4

Effectiveness in Aged Oophorectomized Rats

Because many patients receiving calcitonin treatment are post-menopausal women, an experiment was designed to investigate the effectiveness of the intravaginal preparation of the present invention in aged, oophorectomized rats.

The ovaries of 30-week-old female Wister rats were excised about one month before use in the experiment.

Prior to this experiment, a separate experiment was performed to investigate the susceptibility of aged, oophorectomized rats to porcine calcitonin. Different concentrations of calcitonin were injected into rats in the femoral bicipital muscle, and the decreasing serum calcium was determined. The susceptibility of aged rats to calcitonin was very low, and the largest ratio of decreased serum calcium against control was about 10%; this result differed significantly from the result of the experiment using young rats.

Figure 4:
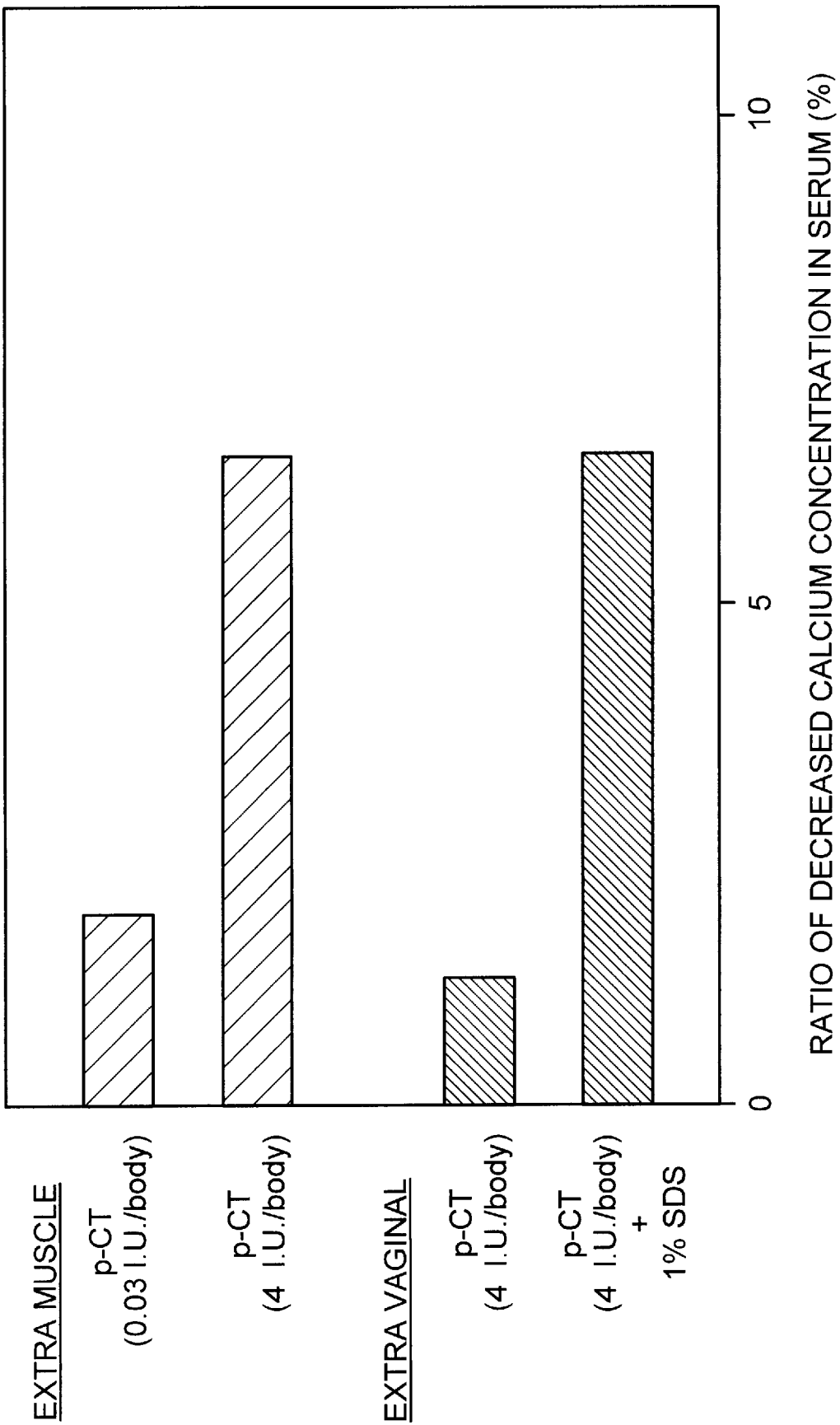
FIG. 4 is a bar graph illustrating that, in administration of porcine calcitonin (P-CT) to aged oophorectomized rat with 1% sodium lauryl sulphate (SDS) showed a similar ratio of decreased serum calcium against control to that of an intramuscular injection group.

Following the procedure of Examples 1 and 2, a dose of 4 I.U. calcitonin per rat was prepared and administered intravaginally by inserting a small cotton ball in the vagina. Following the procedure of Examples 1 and 2, blood was extracted and the blood calcium concentration was determined. As a result of the addition of 1% of SDS to the intravaginal preparation of this invention, the intravaginal group showed a similar ratio of decreased serum calcium against control to that of the intramuscular injection group. See FIG. 4.

EXAMPLE 5

Effect of Sodium Lauryl Sulfate on the Stability of Calcitonin

A porcine calcitonin (P-CT) pharmaceutical preparation according to the invention was prepared by the method described in Examples 1 and 2, and the stability of porcine calcitonin in the resultant preparation was investigated. Thus, 1 ml of 3 mg/ml bovine serum albumin (BSA) solution was added to 40 I.U. of porcine calcitonin, and the mixture was divided into two equal portions. SDS was added to one of the portions to make a final concentration of 0.1 w/v %; and no SDS was added to the other portion. The pH of both of the preparations was then adjusted to pH 5 with acetic acid/sodium acetate buffer (0.1M) solution. These two preparations were then stored at 37° C. for 8 days. The biological activity of calcitonin of the 8-day stored preparations was then investigated using 5-week-old Wister male rats. A dosage of 0.12 I.U./kg calcitonin of these two preparations was administered to the rats by injection into the femoral muscle. One hour after drug administration, blood was extracted from the right external jugular vein, and the blood calcium content was determined. After the 8-day storage period, the biological activity of the preparation containing no SDS decreased to about half that of the freshly made preparation, while the preparation containing SDS did not lose any biological activity after being stored for 8 days. See TABLE 1 below.

TABLE 1

Effect of SDS on Calcitonin Stability

| Treatment | Ratio of Decreased Calcium Concentration Against Control | |
|---|---|---|
| | 0 day | 8 days (at 37° C.) |
| P-CT | 20.7 | 11.1 |
| P-CT + 0.1% SDS | 22.6 | 22.4 |

P-CT(40 I.U.)/0.3% BSA/ml, at pH 5.0

EXAMPLE 6

Stabilizing Effect of Animal Protein on Calcitonin

Using blood calcium decreasing ratio as an indication, the effect of pH and human serum albumin (HSA) on the stability of calcitonin in the preparation of this invention was investigated using 5-week-old male Wister rats.

Figure 5:
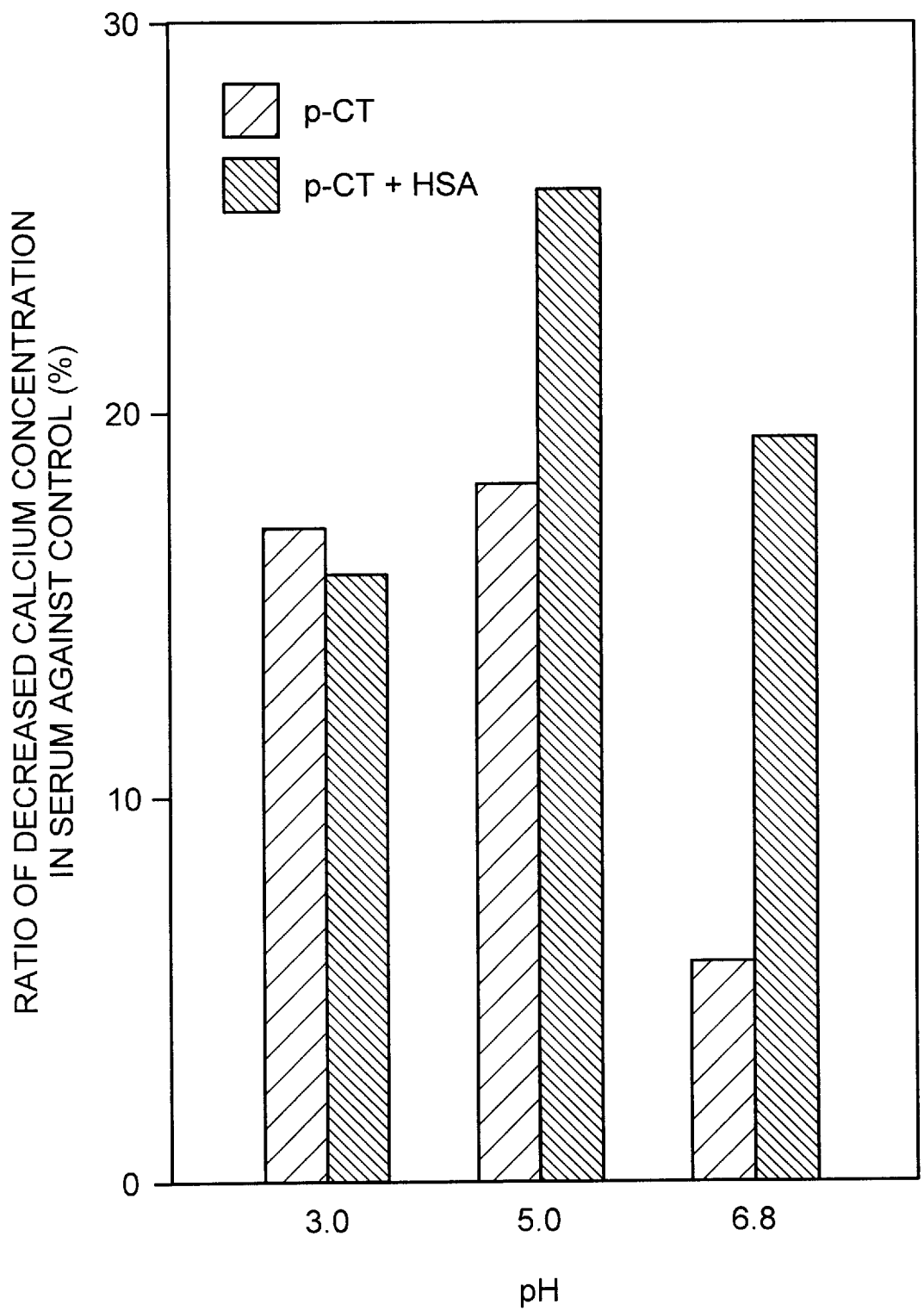
FIG. 5 is a bar graph depicting the effect of human serum albumin (HSA) on the stability of porcine calcitonin (P-CT) at selected pH levels following intramuscular administration to young male rats.

Purified porcine calcitonin (P-CT) was dissolved in 0.1M acetic acid buffer solutions of pH 3.0 and pH 5.0 and 0.1M phosphoric acid buffer solution of pH 6.8 so that each of the solutions contained 0.03 I.U./ml of porcine calcitonin. Each calcitonin solution (pH 3.0, 5.0, 6.8) was divided into two parts. In each case, to one portion of the calcitonin solutions 3 mg/ml of HSA was added, while no treatment was performed on the other portion. The resultant preparations were stored at 4° C. for one week. These calcitonin preparations were then each injected into the femoral bicipital muscle of the rats at a dosage of 0.06 I.U. per kg body weight. An appropriate quantity of blood was extracted from the right external jugular vein, and blood calcitonin concentration was determined with a Calcium C-Test kit. As shown in FIG. 5, calcitonin in the buffer solutions without HSA was stable at pH 3.0 and 5.0, but unstable at pH 6.8. When HSA was added to the preparation, calcitonin in pH 6.8 solution became as stable as calcitonin in a solution of pH 3.0 or 5.0.

EXAMPLE 7

Inhibitory Effect of Sodium Lauryl Sulfate, a Surfactant, on Protease Activity

The inhibitory effect of sodium lauryl sulfate (SDS) on protease activity was investigated in an in vitro study using trypsin, a typical serine protease possessing an optimum pH near neutral, and N-alpha-benzoyl-L-arginine ethyl ester (BAEE), a synthetic substrate. The calcitonin pharmaceutical preparation was prepared according to Examples 1 and 2. The preparation was inserted into the vagina with a small cotton ball. Two hours after the insertion, the inserted cotton ball was removed from the vagina. The vagina was then washed with a fixed quantity of phosphate buffered saline solution, the washed solution was combined with the cotton ball, and the protease activity was determined with BAEE as substrate. The result showed that protease activity decreased about 30% in the 1% SDS added group in comparison with the control group that had no SDS treatment. This result indicated that the SDS incorporated in the pharmaceutical preparation of this invention inhibited calcitonin decomposition by intravaginal protease when the preparation was administered intravaginally. See TABLE 2 below.

TABLE 2

Inhibition of Protease Activity by SDS

| Treatment | BAEE units/mg protein |
|---|---|
| control | 23.4 (100.0) |
| 1% SDS | 6.84 (29.2) |

EXAMPLE 8

Insulin Absorption Enhancing Effect

The oophorectomized rats described in Example 1 were used in this experiment. The insulin pharmaceutical preparation prepared according to this invention was administered intravaginally to the rats, and the change in plasma glucose was investigated. Bovine serum albumin and SDS were added to a solution of 100 U./ml insulin in 0.1M acetic acid/sodium acetate buffer solution to make a final concentration of 3 mg/ml and 1 w/v %, respectively. The pH was adjusted to 5.0 with 0.1M acetic acid/sodium acetate buffer solution. The 5 U. insulin preparation was administered into the vagina of the rat with a small cotton ball. Serum glucose at 2 hours after drug administration was compared with that before drug administration. It was noted that at 2 hours after drug administration, the blood sugar level decreased about 30% in comparison with that prior to drug administration. The findings are summarized in TABLE 3 below.

TABLE 3

Insulin Absorption Enhancing Effect

| Sampling Condition | Glucose Concentration in Serum mg/dl (%) |
|---|---|
| prior to administration | 75 ± 8.5 (100) |
| after 2 hours | 53 ± 24.6 (70.7) |

EXAMPLE 9

The Serum Calcium Profile Following Intravaginal Administration of Suppository and Film Comprising P-CT, SDS, and BSA The pharmaceutical formulations used in this experiment are listed in Table 4.

TABLE 4

| Dosage form | Amount of P-CT/Unit | Absorption Promoter | Protein | Base for Formulation |
|---|---|---|---|---|
| Suppository | 1 I.U. | SDS (1%) | BSA (0.3%) | Glycerogelatin (glycerin:gelatin:H$_2$O 70:20:10) |
| Suppository | 1 I.U. | SDS (1%) | BSA (0.3%) | Polyvinyl alcohol |
| Film | 5 I.U. | SDS (1%) | BSA (0.3%) | Chitosan + HPMC |

Figure 6:
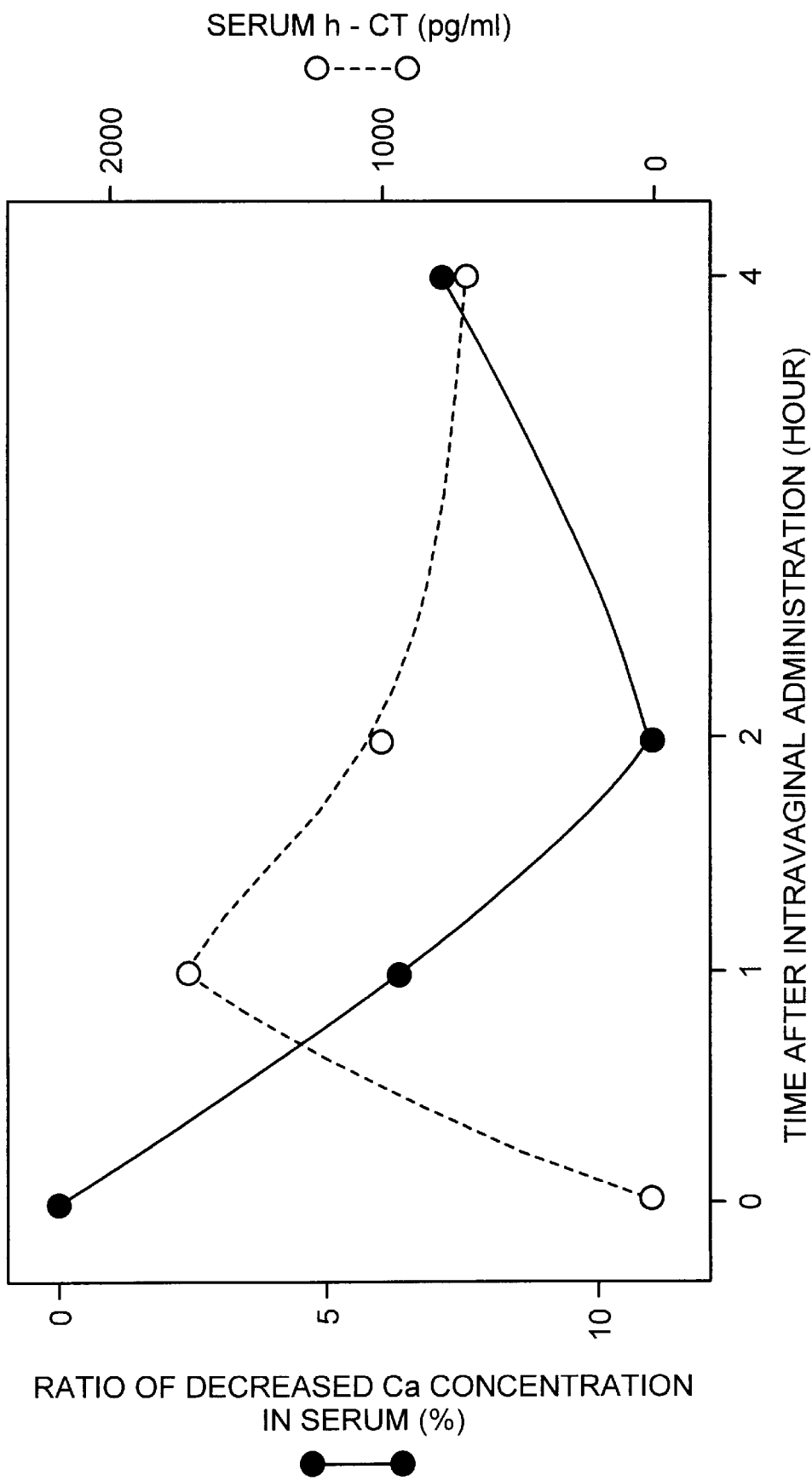
FIG. 6 is a graph showing the serum calcium profile following administration of a suppository and a film comprising porcine calcitonin (P-CT), sodium lauryl sulfate (SDS), bovine serum albumin (BSA) and a nontoxic pharmaceutically acceptable carrier or diluent.

HPMC represents hydroxypropylmethylcellulose. Each formulation listed in Table 4 was administered into the vagina of oophorectomized rats. Blood samples were taken at 2, 4, 8, 12 and 24 hours after vaginal administration, and serum calcium concentration was determined with a Calcium C test kit. The ratio of decreased serum calcium concentration against the control was plotted against time scale. The results are depicted in FIG. 6.

In this experiment, it was found that the formulations in table 4 could decrease the serum calcium concentration similar to the aqueous liquid formulation in example 2.

EXAMPLE 10

Evidence of the Absorption of Human Calcitonin Through Vaginal Mucosa

This experiment was conducted to confirm that H-CT was actually absorbed through rat vaginal mucosa in the presence of sodium caprate and Nonidet P-40.

Figure 7:
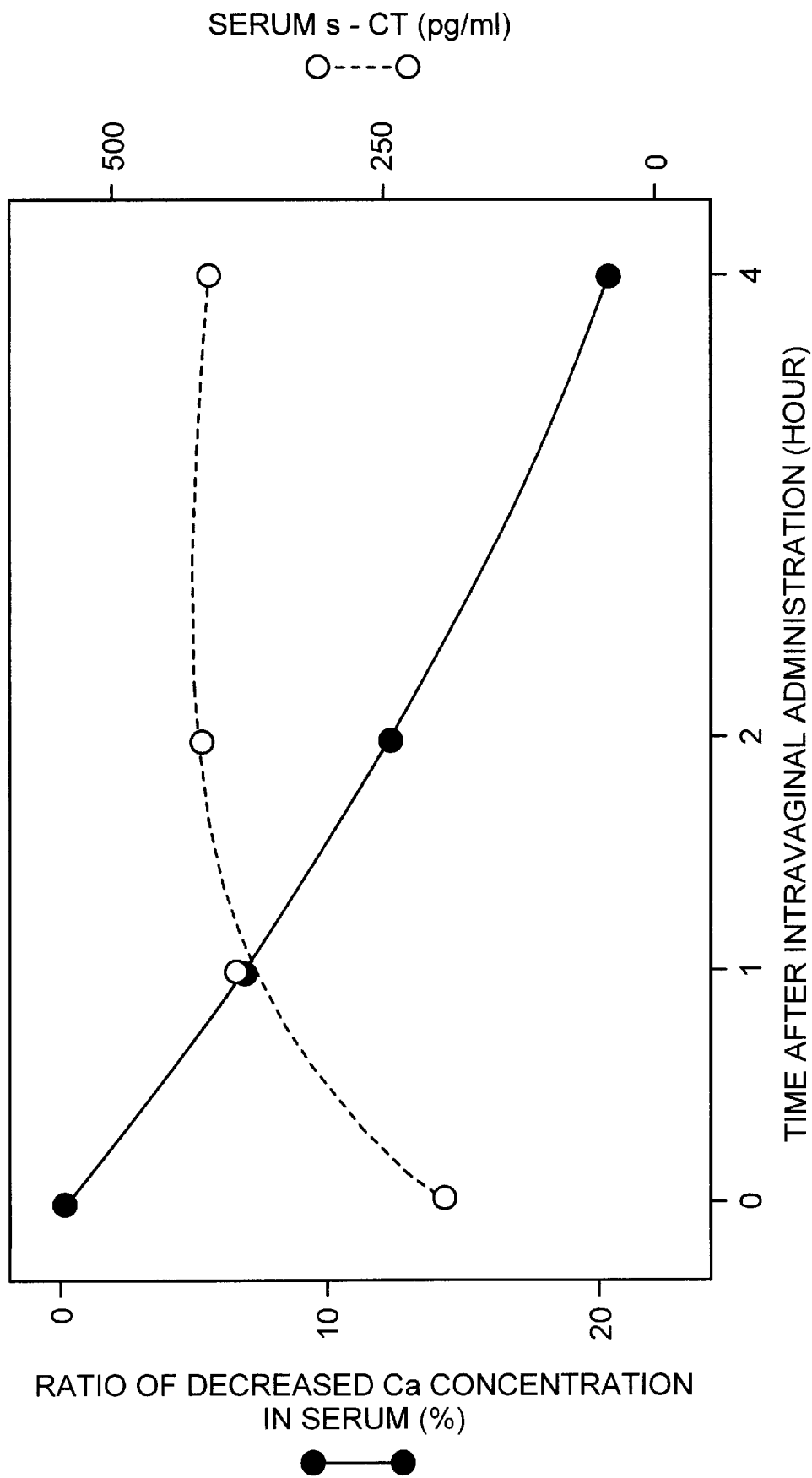
FIG. 7 is a graph showing that the serum calcium decreased correspondingly with the increase of serum human calcitonin (H-CT) following the vaginal liquid administration of H-CT, Nonidet P-40 and sodium caprate and bovine serum albumin to young, oophorectomized female rats.

Oophorectomized rats were used in this experiment in a similar manner as Example 3. 1 mg of H-CT was dissolved in 400 microliters of 0.1M acetate buffer (pH 5) containing 0.3 w/v % bovine serum albumin (BSA) and 1% sodium caprate and 2% Nonidet P-40. 100 microliters of H-CT solution (250 micrograms H-CT) was administered into the vagina of the rat with a small cotton ball. Blood samples were taken from the right external jugular vein of the anesthetized rats at 1, 2 and 4 hours after administration. Serum calcium was determined with a Calcium C test kit. Serum H-CT was also determined by the RIA method using human calcitonin antibody. The results are shown in FIG. 7.

The results indicate that the serum calcitonin increased proportionally to the increase in the dosage of calcitonin administered into the vagina, and the serum calcium decreased correspondingly with an increase in calcitonin dosage. This result indicates that the absorption of H-CT and its biological activity exhibits a dose-dependent response when the composition of this invention containing the combination absorption promoter of sodium caprate and Nonidet P-40 was administered intravaginally.

EXAMPLE 11

The Profile of Serum Calcium and Salmon Calcitonin (S-CT) Concentration After Intravaginal Administration of Suppository Containing S-CT The model animals and experimental procedures are similar to that described in Example 10. The suppositories used in this Example were prepared as follows. 1 mg of S-CT was dissolved in 100 microliters of 0.1M acetate buffer solution (pH 5) containing 1.5 mg of BSA (bovine serum albumin), 10 mg of Nonidet P-40, and 5 mg of sodium caprate. 383 mg of suppository base composed of PEG 4000 (33%), PEG 6000 (47%) and distilled water (20%) was warmed to 45° to 50° C., then mixed well with the S-CT solution using a Vortex mixer for 1 min, then transferred into a brass suppository mold and cooled to approximately 4° C. for 2 hrs. 125 mg of S-CT suppository contained 250 micrograms of S-CT. 250 micrograms of a S-CT suppository was administered into the rat vagina. 1, 2, and 4 hrs after administration, blood samples were taken, and the serum calcium concentration and the serum calcitonin were determined by the same method used in Example 10. The data is listed in FIG. 8.

The results indicate that the absorption of S-CT and its biological activity exhibit a dose-dependent response when the S-CT composition of this invention containing the combination absorption promotor of sodium caprate and Nonidet P-40 was administered intravaginally.

EXAMPLE 12

The Effect of the Combination Type Absorption Promoter

The animal model used in this experiment was basically similar to that of Example 1 except that the age of the oophorectomized rat was different. 100 microliters of the P-CT (4 I.U.) acetate buffer solution containing 0.3 w/v % BSA, the combination absorption promoter (2% polyoxyethylenealkylphenylether and 1% medium chain aliphatic carboxylic acid sodium salt) was administered into the oophorectomized rat vagina with the aid of a cotton ball. 2 hrs. after administration, blood samples were taken and the calcium concentration determined. The ratio of decreased, calcium concentration against control was calculated. The data obtained is summarized in Table 5. Comparison data appears immediately below Table 5. NP-10 represents polyoxyethylene (10) nonylphenylether. NP-15 represents polyoxyethylene (15) nonylphenylether. OP-10 represents polyoxyethylene (10) octylphenylether.

TABLE 5

| | The Invention | |
|---|---|---|
| Combination Absorption Promoters | The Ratio of Decreased Ca$^{++}$ | Age (Weeks) |
| 2% Nonidet P-40 + 1% Na caprylate | 1.5 | 8–9 |
| 2% Nonidet P-40 + 1% Na caprate | 13.7 | 8–9 |
| 2% Nonidet P-40 + 1% Na laurate | 6.5 | 8–9 |
| 2% NP-10 + 1% Na caprate | 5.9 | 32 |
| 2% NP-15 + 1% Na caprate | 3.6 | 32 |
| 2% OP-10 + 1% Na caprate | 4.3 | 32 |

TABLE 5-continued

| | Comparison data | |
|---|---|---|
| Absorption Promoter | The Ratio of Decreased Ca$^{++}$ | Age (Week) |
| 1% Na caprylate | 0.4 | 18 |
| 1% Na caprate | 4.0 | 18 |
| 1% Na laurate | 4.3 | 18 |
| 2% Nonidet P-40 | 0 | 18 |

From the data shown above, the combination of the polyoxyethylenealkylphenylether and medium chain aliphatic carboxylic acid sodium salt gave surprisingly better results in terms of biological response than either of the comparison absorption promoters.

EXAMPLE 13

The Effect of the Combination Type of Absorption Promotor on Elcatonin

The animal model used in this experiment was similar to that of example 1 except for the age of oophorectomized rat. 100 microliters of the solution of elcatonin (400 ng) in 0.1M acetate buffer containing 0.3% w/v BSA and the combination absorption promoter (2% polyoxyethylenealkylphenylether and 1% sodium caprate) was administered into the oophorectomized rat vagina with the aid of cotton ball. 2 hours after administration, the blood samples were taken out and the calcium concentration determined. The ratio of decreased calcium concentration in serum against control was calculated. The data is presented in Table 6.

EXAMPLE 13

| Absorption Promoter | The Ratio of Decreased Ca$^{++}$ Concentration in Serum |
|---|---|
| 2% Nonidet P-40 + 1% Na caprate | 11.9 ± 1.1 |
| 1% Na Caprate | 4.2 ± 0.6 |

The age of rat: 25 weeks old.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. A pharmaceutical composition of matter adapted for intravaginal administration comprising: a stable biologically active polypeptide selected from the group consisting of calcitonin or an analog or derivative thereof, in an amount sufficient to elicit a pharmacological effect when administered intravaginally; an absorption promoter consisting essentially of an effective absorption promoting amount of polyoxyethylene (9) octylphenylether and a medium chain aliphatic carboxylic acid selected from the group consisting of caproic acid, caprylic acid, lauric acid or a salt thereof, the total concentration of said absorption promoter in the composition being between about 0.01 and about 5 w/v %, said concentration being sufficient to enhance absorption of the polypeptide through the vaginal mucosa; and a nontoxic pharmaceutically acceptable carrier or diluent therefor, in a formulation suitable for intravaginal administration.

2. The composition according to claim 1, wherein the stable biologically active polypeptide is eel calcitonin, elcatonin, or an analog thereof.

3. The composition of claim 1, having a pH ranging from about 3 to 7.

4. The composition of claim 1, having a pH ranging from about 4 to 6.

5. The composition according to claim 1, formulated as a liquid.

6. The composition according to claim 1, formulated as a thick viscous gel.

7. The composition according to claim 1, formulated as a suppository, tablet or tampon device.

8. The composition according to claim 1, which further comprises an animal protein, or vegetable protein contained in an amount sufficient to maintain the stability of said calcitonin, analog or derivative thereof.

* * * * *